United States Patent [19]

Tanaka et al.

[11] Patent Number: 5,362,443
[45] Date of Patent: Nov. 8, 1994

[54] METHOD AND APPARATUS FOR DISPOSAL OF MEDICAL WASTE

[75] Inventors: Mitsuyuki Tanaka; Masahiro Michino; Yasutaka Fujihira, all of Sagamihara; Takashi Nakamura, Tokyo; Kisaburo Kohmura, Yatomi; Toshiro Asaoka, Inuyama; Akio Ohya, Nagoya, all of Japan

[73] Assignees: Nippon Metal Industry Co., Ltd., Tokyo; Nissen Corporation, Aichi, both of Japan

[21] Appl. No.: 996,403

[22] Filed: Dec. 23, 1992

[30] Foreign Application Priority Data

Dec. 27, 1991 [JP] Japan .................. 3-357941

[51] Int. Cl.5 .......................... A61L 2/06; A61L 2/24
[52] U.S. Cl. ......................... 422/26; 422/32; 422/33; 422/39; 422/295; 422/309; 241/606
[58] Field of Search ............... 241/606; 422/26-28, 422/32, 33, 39, 295, 303, 309

[56] References Cited

U.S. PATENT DOCUMENTS

| | | | |
|---|---|---|---|
| 2,731,208 | 1/1956 | Dodd | 422/295 X |
| 3,750,966 | 8/1973 | Anderson | 241/606 X |
| 4,365,143 | 12/1982 | Kerber, Jr. | 422/303 X |
| 4,552,720 | 11/1985 | Baker, Sr. et al. | 241/606 X |
| 4,877,990 | 10/1989 | Fiorenzano, Jr. | 219/381 |
| 5,035,858 | 7/1991 | Hold et al. | 422/27 X |
| 5,077,007 | 12/1991 | Pearson | 241/606 X |
| 5,089,228 | 2/1992 | Meijer | 241/606 X |
| 5,091,158 | 2/1992 | Drauschke et al. | 422/295 |
| 5,116,574 | 5/1992 | Pearson | 241/606 X |
| 5,119,994 | 6/1992 | Placzek | 422/26 X |
| 5,122,344 | 6/1992 | Schmoegner | 422/32 X |
| 5,130,092 | 7/1992 | Liu | 422/38 X |
| 5,147,613 | 9/1992 | Heilmann et al. | 422/28 X |
| 5,185,126 | 2/1993 | Adamski et al. | 422/38 |

FOREIGN PATENT DOCUMENTS

| | | |
|---|---|---|
| 0372664 | 6/1990 | European Pat. Off. |
| 0383553 | 8/1990 | European Pat. Off. |
| 2226912 | 12/1973 | Germany |
| 9116084 | 10/1991 | WIPO |
| 9212738 | 8/1992 | WIPO |

*Primary Examiner*—Donald E. Czaja
*Assistant Examiner*—Milton I. Cano
*Attorney, Agent, or Firm*—Wenderoth, Lind & Ponack

[57] ABSTRACT

A method and an apparatus for simply disposing medical waste from a medical institution on site. The method comprises crushing medical waste in a closed container, exhausting air out of the container, sterilizing the air before releasing it into the atmosphere, and filling the container with a high-pressure steam having a temperature between 110° C. and 150° C. to sterilize the crushed medical waste. The apparatus is equipped with a pressure container having at least one air-tight seal, an internal waste crushing mechanism such as blades, an internal supply of steam, a valve for exhausting air from the container, and an air sterilizer for the exhausted air.

12 Claims, 1 Drawing Sheet

METHOD AND APPARATUS FOR DISPOSAL OF MEDICAL WASTE

FIELD OF THE INVENTION

The present invention relates to a method for disposing of contagious or infectious medical waste from medical activities by sterilizing it and decreasing the volume thereof, and an apparatus therefor. In particular, the present invention relates to a method for disposing of medical waste suitable for sterilizing contagious or infectious waste having the form of a pipe or a tube and decreasing the volume thereof, and an apparatus therefor.

DESCRIPTION OF RELATED ART

Waste from medical activities is often contaminated by contagious or infectious pathogenic organisms, and careless handling of such medical waste may cause diseases. Therefore, medical waste, particularly contagious or infectious medical waste is classified in a medical institution, and it is collected, transported and incinerated by a specialized disposal expert.

However, the number of such specialized disposal experts is not large. On the other hand, in recent years, so-called disposable medical instruments typified by a disposable syringe have been being increasingly used from the viewpoint of safety and medical activity efficiency. The amount of contagious or infectious waste from medical institutions thus increases year after year. Therefore, the disposal of contagious or infectious waste requires a high cost, and leads to an increase in the cost of medical activities.

Further, the collection, transportation and disposal of medical waste by a disposal expert involves a risk of the medical waste being spread by an accident during any one of these activities. There is a method of monitoring the medical waste disposal by means of a manifest system. However, it cannot be said that this monitoring method is fully satisfactory concerning the final disposal.

It is therefore desired to develop a method and an apparatus for the reliable disposal of contagious or infectious medical waste within a medical institution (hereinafter referred to as "in-institution disposal") at a low cost without causing a risk in transportation.

As a method of in-institution disposal, there are known a variety of methods using crushing treatment, incineration, heat treatment and sterilization with a liquid chemical, and there are some proposed methods and apparatus for realizing the in-institution disposal. However, these methods involve the following problems.

Although being proper as the treatment for decreasing the volume of medical waste before delivery thereto to a disposal expert, the crushing treatment does not include sterilization. Therefore, the crushed waste is still contagious or infectious, and special handling is required. Further, an apparatus used for crushing medical waste may be contaminated with contagious or infectious pathogenic organisms, and special handling thereof is therefore required.

The incineration is the most reliable from the viewpoint of sterilization. Since, however, most medical instruments are formed of plastic materials, the plastic materials decompose when incinerated to generate gases containing harmful substances. That is, a secondary contamination problem occurs, and it is required to use a large apparatus for treating the exhaust gases. Further, the incinerator requires a wide place where it is to be installed, and it is therefore not proper for use in hospitals in cities.

The heat treatment which is a step before incineration is classified into dry heating and wet heating. In dry heating, a sterilization effect is obtained only when the heat treatment is carried out at a temperature of about 200° C. or higher for 1 hour or more until the inside of the medical waste is fully heated. Further, most of plastic materials generate harmful decomposition gases at the above temperature, and the treatment of the decomposition gases is again a problem. In wet heating with high-pressure steam, it is said that the sterilization is completed by exposing medical waste to the steam at 121° C. for 20 minutes. At this temperature, plastic materials forming medical instruments are stable, and cause no secondary contamination problem. However, contagious or infectious waste medical instruments often have the form of a pipe or a tube, and one end thereof is sometimes closed or the form itself is very complicated, as can be understood from a syringe cylinder, a dialysis instrument, a blood piping system, and the like. Therefore, high-pressure steam would not fully reach the interiors of these waste instruments, and it is therefore hard to say that such instruments can be fully sterilized even if the wet heating is carried out at the above temperature for the above period of time.

In the sterilization using a liquid chemical, the chemical itself is harmful to a human body, and handling of the chemical and disposal of the wasted chemical may cause secondary contamination. Safety measures and disposal of liquid waste generate additional costs. Moreover, like the case of sterilization using high-pressure steam, the chemical does not fully reach the interiors of waste materials having the form of a pipe or a tube, and it is therefore difficult to achieve complete sterilization.

SUMMARY OF THE INVENTION

It is an object of the present invention to provide a method and an apparatus for simply disposing medical waste from a medical institution without taking it out of the medical institution.

It is another object of the present invention to provide a method and apparatus for sterilizing contagious or infectious medical waste from a medical institution at a relatively low temperature for a short period of time and for decreasing the volume of the medical waste.

It is further another object of the present invention to provide a method and an apparatus for disposing of contagious or infectious medical waste from a medical institution, the method and apparatus being particularly suitable for in-institution disposal of contagious or infectious medical waste having the form of a pipe or a tube such as a syringe cylinder, a dialysis instrument and a blood piping system.

According to the present invention, there is provided a method of disposing of medical waste, which comprises crushing medical waste in a closed container, exhausting air out of the container, sterilizing the air before releasing it into atmosphere, and filling the container with a high-pressure steam having a temperature between 110° C. and 150° C. to sterilize the crushed medical waste.

According to the present invention, there is also provided an apparatus for disposing of medical waste, which is equipped with a pressure container having at least one opening portion with an air-tightly closing means, a means of crushing medical waste, a means of supplying steam, a means of exhausting air out of the pressure container and a means of sterilizing the exhausted air, the means of crushing medical waste and the means of supplying steam being positioned within the pressure container.

BRIEF DESCRIPTION OF DRAWING

Figure appended to the present specification is a schematic view showing an apparatus for disposing medical waste, provided by the present invention.

DETAILED DESCRIPTION OF THE INVENTION

Figure 1:
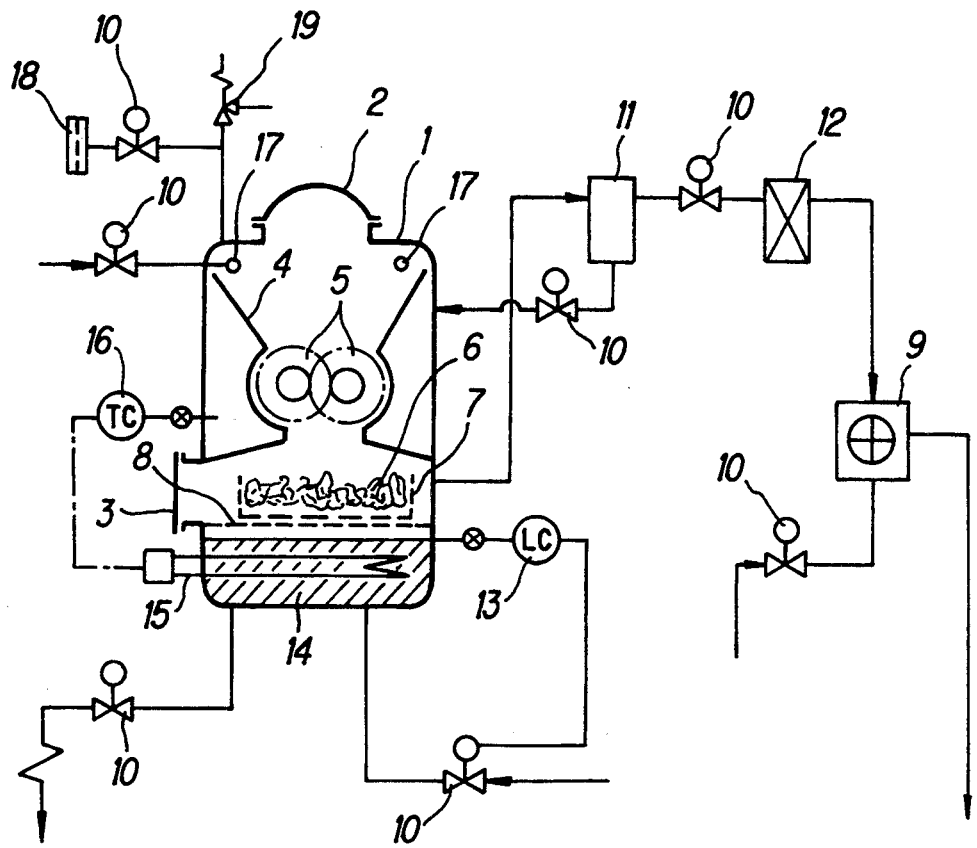

In the method of the present invention, the high-pressure steam is required to have a temperature between 110° C. and 150° C. When the temperature is lower than 110° C., the sterilization treatment takes an impractically long time to obtain a sufficient sterilization effect. When it is higher than 150° C., the required pressure withstanding strength of the container is too high to produce the container at a reasonable cost. Further, when it is higher than 150° C., some of waste medical instruments start to decompose, and secondary contamination may occur. When the high-pressure steam has a temperature in the above range, it is preferred to keep the container filled with the high-pressure steam for at least 10 minutes to obtain a sufficient sterilization effect.

In the method of the present invention, the crushing treatment is carried out before the sterilization treatment with a high-pressure steam for the following reason, When waste medical instruments having the form of a pipe or a tube and having closed end(s) or a complicated form such as a syringe cylinder, a dialysis instrument, a blood piping system, and the like which are internally contaminated with blood are subjected to the sterilization treatment with a high-pressure steam, the steam hardly reaches the interiors of these instruments, and it cannot be said that the sterilization by wet heating is completed even if they are treated at the above temperature for the above period of time. That is, waste medical instruments need to be crushed before the sterilization treatment with a high-pressure steam for positively exposing their interior portions contaminated with blood to the high-pressure steam.

The crushing treatment is carried out before the sterilization treatment as described above. As a result, the internal wall of the container and the elements (e.g., blade, etc.) of crushing means may be contagious or infectious, and they are also required to be sterilized together with medical waste. For sterilizing these portions and crushed medical waste efficiently for a short period of time, therefore, they are sterilized with a high-pressure steam within the container without taking the crushed medical waste out of the container. Therefore, the crushing means, the steam supplying means, etc., are positioned within the container, and the container has a structure in which it can be air-tightly closed to fill it with a high-pressure steam.

For filling the container with a high-pressure steam, it is required to exhaust air out of the container. However, the air to be exhausted out of the container contains or may contain contagious or infectious microorganisms spread by crushing medical waste. In the present invention, the air is therefore sterilized before releasing it into atmosphere. This sterilization can be carried out by filtering, heating or chemically oxidizing, and the like, although it shall not be limited thereto.

The accomplishment of the aforementioned method is a characteristic feature of the medical waste disposal apparatus of the present invention. The apparatus of the present invention is equipped with a pressure container having at least one opening portion with an air-tightly closing means, the opening portion being an inlet for medical waste and/or an outlet for crushed and sterilized medical waste, a means (e.g., a blade) of crushing medical waste, a means (e.g., a heater) of supplying steam, a means (e.g., a pump) of exhausting air out of the pressure container and a means of sterilizing the exhausted air, the means of crushing medical waste and the means of supplying a steam being positioned within the pressure container.

The apparatus of the present invention is required to have a pressure container having an air-tightly closable structure, and it is also required to have a means of crushing medical waste and a means of supplying steam such as a heater within the pressure container. Further, the apparatus of the present invention is required to have a means (e.g., a pump) of exhausting air out of the pressure container and a means of sterilizing the exhausted air.

Examples of the means of crushing medical waste include a crushing device equipped with a blade having the form of a mixer blade, a crushing device having the system of a ball mill, a crushing device for shearing between a monoaxially rotating blade and a fixed blade and a crushing device for shearing between biaxially rotating blades. The crushing means used in the present invention is required to be capable of crushing medical waste such that the interior thereof is fully sterilized in the sterilization with a high-pressure steam even if the medical waste has the form of a pipe or a tube, has a closed end or has a complicated form. The crushing means is also required to be suitable for in-institution disposal without making much noise. It is required to be simple in mechanism and suitable for crushing within a closed container. It is required to be strong and durable in structure and easy in maintenance. It is further required not to take a long time to finish the crushing.

In the apparatus of the present invention, the steam supplying means may be positioned outside the pressure container. In this case, the steam supplying means may be a device being connected to the pressure container through a pipe, etc., and internally having a steam generating means such as a heater, or a device having a valve, etc., through which an externally generated steam is introduced into the pressure container.

In the method and apparatus provided by the present invention, contagious or infectious medical waste can be reliably sterilized at a relatively low temperature for a short period of time due to the employment of a high-pressure steam sterilization method. Further, there is no risk of secondary contamination being caused by a decomposition gas to be generated by plastic materials forming medical instruments. Moreover, since medical waste is crushed before the high-pressure steam sterilization step, medical waste having the form of a closed-end pipe or tube or a complicated form can be crushed so that the steam reliably reaches the interiors of such medical waste in the high-pressure steam sterilization step. Further, the volume of medical waste can be decreased.

Further, when the pressure container is filled with a high-pressure steam, air which is or may be contaminated due to the crushing treatment within the container is sterilized before releasing it into atmosphere. Therefore, there is no risk of contagious or infectious microorganisms contained in the air causing secondary contamination.

The crushing of contagious or infectious medical waste and the high-pressure steam sterilization are carried out in the same pressure container. Therefore, the wall of the container and the other devices within the container which may be contaminated due to a contact with contagious or infectious medical waste are sterilized together with medical waste. As a result, when the pressure container is opened after the disposal, no contagious or infectious microorganisms come out and the inside of the container is safe. Further, since the crushing and sterilization are carried out in the same container, the disposal process and apparatus are simplified, and the costs for manufacturing the apparatus and for the disposal of medical waste can be decreased.

After contagious or infectious medical waste is sterilized, the crushed medical waste, the internal wall of the container, the devices in the container and water remaining in the container have all been sterilized. Therefore, the sterilized crushed medical waste taken out of the container is no longer contagious or infectious and can be handled as ordinary industrial waste. As a result, the cost for the final disposal of the waste is by far less expensive than the cost for the disposal of contagious or infectious medical waste. Further, there is a decreased risk of contagious or infectious medical waste spreading into atmosphere when it is collected, transported and disposed of according to the present invention.

As explained above, according to the method and apparatus of the present invention, contagious or infectious medical waste from medical institutions can be reliably sterilized, volume-decreased and converted to non-contagious or non-infectious industrial waste with an in-expensive institution apparatus at a relatively low temperature for a short period of time without taking it out of the medical institutions. There is no risk of exhausted air causing secondary contamination, and the cost for the disposal can be decreased.

EXAMPLES

The present invention will be described further in detail by reference to a drawing. FIG. 1 schematically shows an apparatus for disposing of medical waste, provided by the present invention. The constitution of the apparatus for disposing of medical waste and the method of disposing of medical waste, provided by the present invention, will be explained hereinafter on the basis of the drawing.

Example 1

Medical waste from medical activities is fed to a container 1 through an inlet 2 which is one opening of the container 1 formed so as to endure a high-pressure steam. The container 1 has an outlet 3 as another opening. These two openings are structured to be air-tightly closed for the introduction of a high-pressure steam into the container. The fed medical waste passes along a hopper 4 positioned within the container 1 and it is stacked on rotary blades 5 for crushing by biaxial rotary shearing. Then, the inlet 2 is closed to prevent the spread of the medical waste out of the container 1, and the rotary blades 5 are rotated with a motor (not shown) positioned outside the container 1, whereby the medical waste is crushed, and the resultant pieces 6 are stacked on a receiving pan 7 on a receiving bed 8.

The above device fox crushing by biaxial rotary shearing may be a device which has two rollers whose rotation axes are parallel or nearly parallel with each other, the rollers having blade(s) for shear fracture, and which shear-fractures or crushes waste between the two rollers being mutually engaged while being rotated. The crushing device of the present invention shall not be limited to this biaxial shear crushing device. The receiving pan 7 and the receiving bed 8 are formed of perforated metal (porous plates) so that high-pressure steam can easily pass. The perforated metal as a material therefor is one embodiment, and the receiving pan and the receiving bed may be formed of any suitable material.

Then, a pump 9 positioned outside the container 1 and connected to the container 1 through a tubing is actuated to suck air from the interior of the container 1. A valve 10 positioned on a tubing as required is opened or closed as needed. The valve 10 is similarly opened or closed as needed in processing steps to be carried out hereinafter, and its explanation is omitted. The sucked air is released into the atmosphere through a sterilization filter 11 positioned on the tubing. As a result, the air which may contain contagious or infectious microorganisms in the container 1 does not cause secondary contamination.

Although this Example uses a sterilization filter 11, the above sterilization treatment may be carried out by a variety of methods using filtering, heating, chemical oxidation, and the like. Numeral 12 indicates a deodorizer using, e.g., an activated carbon adsorption method. The placement of the deodorizer is optional. When air sucked from the interior of the container 1 has an unpleasant odor before or after the sterilization with a high-pressure steam, the deodorizer is placed to remove the odor from the air before releasing the air into atmosphere. When the sterilization filter is replaced with a sterilizer using heating, the air passing the sterilizer can be sterilized and deodorized at the same time.

Water 14, which is introduced into the container 1 from an external water source (not shown) and whose level is controlled with a water controller 13, is heated with heater 15 to fill the container 1 with a high-pressure steam. For example, the high-pressure steam having a temperature of 121° C. is maintained for 20 minutes, whereby the sterilization of the crushed waste, the internal wall of the container and other devices is finished. The temperature inside the container 1 is controlled with a temperature controller 16.

After the sterilization treatment is finished, water is jetted out through a nozzle 17 positioned within the container to cool the container and crushed waste. External air is introduced into the container through an air filter 18 to bring the interior of the container into atmospheric pressure. The outlet 3 is opened, and the receiving pan 7 is taken out to discharge the sterilized crushed pieces 6. The water 14 in the container 1 is also discharged through a tubing. The container 1 is naturally manufactured so as to withstand the pressure of the high-pressure steam, while it is also provided with a safety valve 19 to cope with an abnormal increase in the pressure.

In the apparatus of this Example, the above procedures form one cycle for disposing medical waste.

Further, the following Example was carried out for examining whether the sterilization of contagious or infectious medical waste could be fully achieved according to the method and apparatus for disposing medical waste, provided by the present invention.

Example 2

Bacterial spores were sealed in dialyzers used for dialysis of a patient having renal insufficiency, and three lots (each lot consisting of 20 dialyzers) were disposed of by the same apparatus as that described in Example 1 according to the same method as that described in Example 1. Each lot was sterilized with a high-pressure steam having the following temperature for a following period of time.

| Lot No. | 1 | 2 | 3 |
| --- | --- | --- | --- |
| Temperature (°C.) | 115 | 121 | 126 |
| Time (minute) | 30 | 20 | 15 |

The sterilization after the above disposal was determined by an aseptic test method according to Japanese Pharmacopoeia, in which the sterilized crushed dialyzer pieces, discharged water and discharged air were respectively cultured in thioglycolic acid culture media at 37° C. for 7 days and the resultant media were examined. As a result, no bacteria was detected in the sterilized crushed dialyzer pieces, discharged water and discharged air with regard to each lot. This result shows that medical waste having the form of a closed end pipe whose interior is contaminated with contagious or infectious blood such as a dialyzer can be reliably disposed of by the method and apparatus for disposing medical waste, provided by the present invention. Further, the volume of the treated dialyzers was decreased to about ½ of that of the dialyzers before the treatment.

What is claimed is:

1. A method for disposing of medical waste, comprising carrying out the successive steps of:
    a. shearing medical waste in a closed container having an internal wall with a device to expose an interior portion of the medical waste to direct contact with a high-pressure steam,
    b. exhausting air out of the container and sterilizing the air before releasing it into the atmosphere, and
    c. generating and filling the container with the high-pressure steam having a temperature between 110° C. and 150° C. to sterilize the sheared medical waste, the internal wall of the container and the device to expose the interior portion of the medical waste within the container.

2. A method according to claim 1, wherein the sheared medical waste is sterilized by the high-pressure steam for at least 10 minutes.

3. A method according to claim 1, wherein the other device is a means for crushing medical waste.

4. A method according to claim 1, wherein the air is sterilized by at least one means selected from the group consisting of filtering means, heating means and chemical oxidation means.

5. An apparatus for disposing of medical waste having non-exposed interior portions, comprising a pressure container having at least one top opening portion with a means for closing said at least one top opening providing for an airtight closing, a means for crushing medical waste which is capable of shearing the medical waste to expose the interior portions of the medical waste to direct contact with high-pressure steam, a means for generating steam below said crushing means, said steam generating means comprising water filled in a lower portion of the pressure container and a heater provided within the water, a means for exhausting air out of the pressure container and a means for sterilizing the exhausted air, wherein the means for crushing medical waste and the means for generating steam are positioned within the pressure container.

6. An apparatus according to claim 5, wherein the pressure container has an opening formed in an upper portion of the pressure container which is an inlet for feeding medical waste therein and another opening formed in a lower portion of the pressure container which is an outlet for discharging the sheared and sterilized medical waste.

7. An apparatus according to claim 5, wherein the pressure container has a movable receiving pan for receiving sheared medical waste, the receiving pan being positioned above the water and having a plurality of pores at least in a bottom thereof.

8. An apparatus according to claim 5, wherein the means for exhausting air comprises a pipe communicating with the pressure container and an air-sucking pump connected to the pipe.

9. An apparatus according to claim 8, wherein a deodorizer is further placed between the means of sterilizing the exhausted air and the sucking pump.

10. An apparatus according to claim 9, wherein the pressure container further has a means of introducing air to bring a pressure within the pressure container back to atmospheric pressure.

11. An apparatus according to claim 5, wherein the means for sterilizing the exhausted air is at least one means selected from the group consisting of a filtering means, a heating means and a chemical oxidation means, positioned in a pipe connecting the pressure container and a sucking pump.

12. An apparatus according to claim 5, wherein the pressure container further has a means for jetting water to cool the steam.

* * * * *